US00PP30558P3

(12) United States Plant Patent
Danziger

(10) Patent No.: US PP30,558 P3
(45) Date of Patent: Jun. 4, 2019

(54) ***CRASPEDIA* PLANT NAMED 'DCRAGOLFBY'**

(50) Latin Name: *Craspedia globosa*
Varietal Denomination: DCRAGOLFBY

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 68 days.

(21) Appl. No.: 15/732,043

(22) Filed: Sep. 8, 2017

(65) Prior Publication Data

US 2019/0082574 P1 Mar. 14, 2019

(51) Int. Cl.
*A01H 5/02* (2018.01)
*A01H 6/56* (2018.01)

(52) U.S. Cl.
USPC ..... Plt./263.1
CPC ..... *A01H 6/56* (2018.05)

(58) Field of Classification Search
USPC ..... Plt./263.1
See application file for complete search history.

*Primary Examiner* — Anne Marie Grunberg
(74) *Attorney, Agent, or Firm* — Cassandra Bright

(57) ABSTRACT

A new and distinct *Craspedia* cultivar named 'DCRAGOLFBY' is disclosed, characterized by early flowering and a higher than average amount of flowering stems per plant. Plants can tolerate high temperatures to 35 degrees C. The new variety is a *Craspedia*, normally produced as an outdoor garden or container plant.

2 Drawing Sheets

Figure 1:
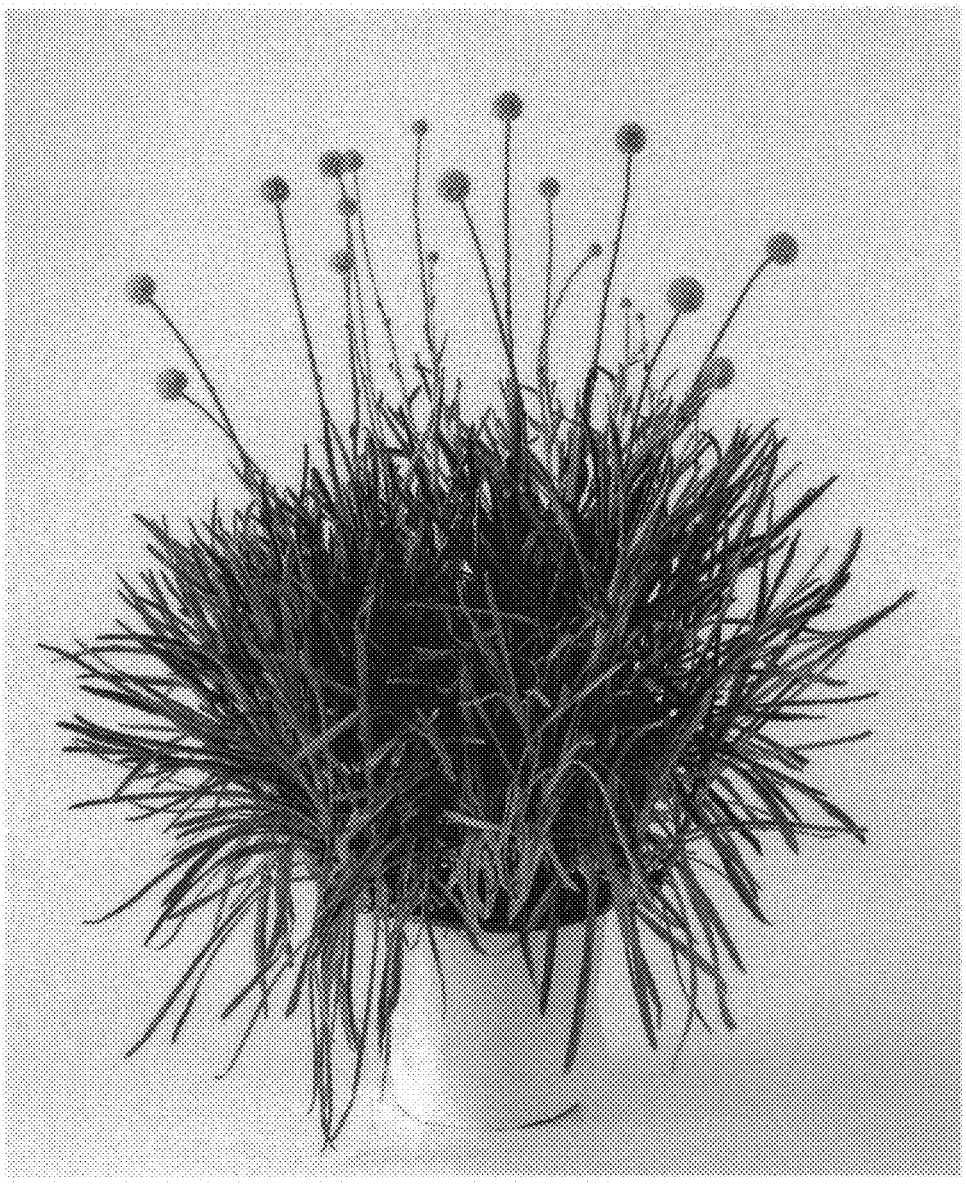

Latin name of the genus and species: *Craspedia globosa*. Variety denomination: 'DCRAGOLFBY'.

BACKGROUND OF THE INVENTION

The new *Craspedia* cultivar is a product of a planned breeding program conducted by the inventor, Gavriel Danziger in Nir-Zvi, Israel. The self-pollination resulting in this new variety was made during March of 2012.

The parent is the unpatented, propriety variety referred to as *Craspedia* 'CR.12-165'. The new variety was selected in March 2013 by the inventor in a group of seedlings resulting from the 2012 self-pollination, in a greenhouse in Nir-Zvi, Israel.

Asexual reproduction of the new cultivar 'DCRAGOLFBY' was first performed by vegetative cuttings during December of 2009, at a greenhouse in Nir-Zvi, Israel. Subsequent propagation by vegetative cuttings has shown that the unique features of this cultivar are stable and reproduced true to type in multiple successive generations.

SUMMARY OF THE INVENTION

The cultivar 'DCRAGOLFBY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCRAGOLFBY' These 1. Early flowering.
2. Increased quantity of flowering per plant.
3. Very good heat tolerance.

PARENT COMPARISON

Plants of the new cultivar 'DCRAGOLFBY' are similar to plants of the parent in most horticultural characteristics, however, plants of the new cultivar 'DCRAGOLFBY' differ in the following;

1. The new variety begins flowering approximately 3 weeks before the parent variety.
2. The parent variety produces on average 6 flowering stems, the new variety produces on average 10 flowering stems.
3. The new variety tolerates temperatures up to 30 to 35° C., the parent variety cannot tolerate temperatures this high.

COMMERCIAL COMPARISON

Plants of the new cultivar 'DCRAGOLFBY' can be compared to the unpatented commercial variety *Craspedia* 'DPBALGLOBE'. These varieties are similar in most horticultural characteristics however, 'DCRAGOLFBY' differs in the following:

1. 'DPBALGLOBE' has larger flowers than the new variety.
2. 'DPBALGLOBE' flowers approximately 2 to 4 weeks later than the new variety.
3. 'DPBALGLOBE' produces longer foliage than the new variety.
4. Plants of 'DPBALGLOBE' are taller than plants of the new variety.

Plants of the new cultivar 'DCRAGOLFBY' can also be compared to the unpatented commercial variety *Craspedia* 'DPBALPOP'. These varieties are similar in most horticultural characteristics; however, 'DCRAGOLFBY' differs in the following:

1. 'DPBALPOP' produces on average 13 flowering stems per plant, whereas new variety produces on average 10 flowering stems per plant.
2. 'DPBALPOP' is taller than the new variety.
3. 'DPBALPOP' flowers 3 to 5 weeks later than the new variety.
4. Flower diameter of 'DPBALPOP' is larger than the flower diameter of the new variety.

5. 'DPBALPOP' has a flat flower head shape while 'DCRAGOLFBY' has a round flower head shape

BRIEF DESCRIPTION OF THE PHOTOGRAPHS

The accompanying photograph in FIG. 1 illustrates in full color a typical plant of 'DCRAGOLFBY' grown in 25 cm pots outdoors in Nir-Zvi, Israel.

Figure 2:
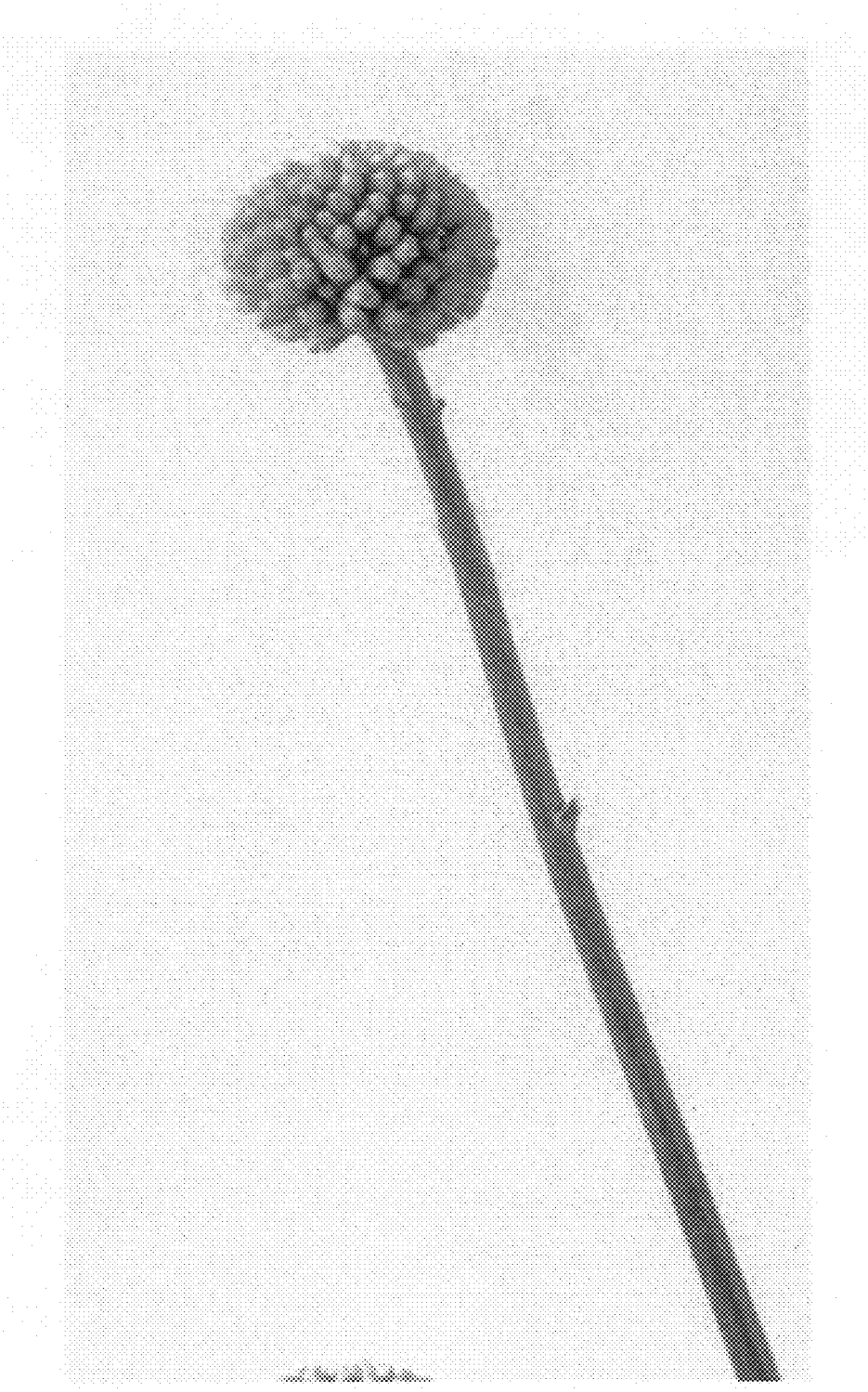

FIG. 2 illustrates in full color a close up view of a typical inflorescence of 'DCRAGOLFBY'. Age of the plant photographed is approximately 11 weeks from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color comparators are made to The Royal Horticultural Society Mini Colour Chart 2005 except where general terms of ordinary dictionary significance are used. The following observations and measurements describe 'DCRAGOLFBY' plants grown outdoors in Nir-Zvi, Israel, under natural lighting. The plants were approximately 95 days old from 3 rooted cuttings in a 25 cm pot. The growing temperature ranged from approximately 23° C. to 30° C. during the days, 15° C. to 22° C. during the nights. Measurements and numerical values represent averages of typical plant types.

Botanical classification: *Craspedia globosa* 'DCRAGOLFBY'.

PROPAGATION

Time to initiate rooting: 21 to 28 days at approximately 20° to 30° C.

Root description: Fibrous. Medium brown in color, not accurately measured with R.H.S. chart.

PLANT

Growth habit: Mounded, grassy base with long flowering stems held above foliage.

Height: Approximately 29 cm to top of foliage. Approximately 60 cm to top of foliage.

Plant spread: Approximately 30 cm.

Growth rate: Medium.

Branching characteristics: Basal foliage, no branching.

FOLIAGE

Leaf:

- *Arrangement*.—Clumping.
- *Average length*.—Approximately 17 cm.
- *Average width*.—Approximately 0.5 cm.
- *Shape of blade*.—Linear.
- *Apex*.—Narrowly acute.
- *Base*.—Clasping.
- *Margin*.—Involute.
- *Texture of top surface*.—Sericeous.
- *Texture of bottom surface*.—Sericeous.
- *Appearance top surface*.—Matte.
- *Appearance bottom surface*.—Matte.
- *Color*.—Young foliage upper side: Near Green N138B. Young foliage under side: Near N138B. Mature foliage upper side: Near N138B. Mature foliage under side: Near N138B.
- *Venation*.—Type: Venation color upper side: Near Green N138B. Venation color under side: Near Green N138B.

FLOWER

Bloom period: Year round in Israel.

Time to flowering from rooted cutting: Approximately 6-8 weeks.

Rate of flower opening: Approximately 1 week from bud to fully opened flower.

Approximate quantity of flowers per plant: Approximately 6 mature inflorescence, showing yellow color and 4 immature, pale yellow inflorescence per plant.

Inflorescence longevity on plant: At least 4 weeks before any significant change is observed.

Inflorescence: Rounded capitulum.

- *Diameter of entire inflorescence*.—Approximately 2.2 cm.
- *Depth of entire inflorescence*.—Approximately 2.2 cm.
- *Receptacle shape*.—Round.
- *Receptacle height*.—Average 2 cm.
- *Receptacle diameter*.—Average 2.2 cm.
- *Receptacle color*.—Near 150D RHS.

Bud:

- *Bud shape*.—Elongated sphere.
- *Bud length*.—Approximately 5 mm.
- *Bud diameter*.—Approximately 2.5 mm.
- *Bud color*.—Base near Yellow-Green 145C, upper section near Green-Yellow 1B.

Flower:

- *Diameter of entire flower*.—Approximately 6 mm.
- *Depth of flower*.—Approximately 2.5 mm.

Petals:

- *Quantity*.—5.
- *Length*.—Approximately 0.2 cm.
- *Width*.—Approximately 0.2 cm.
- *Shape*.—Tubular.
- *Apex shape*.—Acute.
- *Base*.—Tapered.
- *Margin*.—Entire.
- *Color*.—When opening: Upper surface: Near Yellow 7A. Lower surface: Near Yellow 7A. Fully opened: Upper surface: Near Yellow 7A. Lower surface: Near Yellow 7A. Flower Color Fading: No.

Bractcole:

- *Quantity*.—4 per flower.
- *Length*.—Average 0.35 cm.
- *Diameter*.—Approximately 0.1 cm.
- *Shape*.—Oval.
- *Texture*.—Smooth.
- *Color*.—Near Green-Yellow 1D.

Phyllaries/involucral bracts: Not Present.

Fragrance: Not observed.

Peduncle:

- *Length*.—Longest average 70 cm. Shortest average 25 cm.
- *Diameter*.—Approximately 0.3 cm.
- *Texture*.—Sericeous.
- *Color*.—Near Yellow-Green 147B.
- *Orientation*.—Approximately 90 degree angle from rosette.

REPRODUCTIVE ORGANS

Stamens:
*Number*.—1.
*Filament length*.—Approximately 0.1 cm.
Anthers:
*Length*.—Approximately 0.15 cm.
*Shape*.—Tubular.
*Color*.—Near Yellow 7A.
*Pollen*.—Color: Near Yellow 7A.
Pistil:
*Number*.—1.
*Length*.—Approximately 0.3 cm.
*Style*.—Length: Approximately 0.05 cm. Color: Near Yellow 7A.
*Stigma*.—Shape: Bilobed. Color: Near Yellow 7A.

OTHER CHARACTERISTICS

Seeds and fruits:
*Shape*.—Tubular achenes.
*Color*.—Near Greyed-White 156B.
*Size*.—0.3 cm on 0.15 cm.
Disease/pest resistance: Neither resistance nor susceptibility to normal diseases and pests of *Craspedia* has been observed.
Temperature tolerance: Approximate temperature range of 5° C. to 35° C.
Drought tolerance: Not tolerant to drought.

What is claimed is:

1. A new and distinct cultivar of *Craspedia* plant named 'DCRAGOLFBY' as herein illustrated and described.

* * * * *